United States Patent
Omi

(10) Patent No.: US 10,825,189 B2
(45) Date of Patent: Nov. 3, 2020

(54) RADIATION IMAGING APPARATUS, RADIATION IMAGING SYSTEM, RADIATION IMAGING METHOD, AND COMPUTER-READABLE MEDIUM THEREFOR

(71) Applicant: CANON KABUSHIKI KAISHA, Tokyo (JP)

(72) Inventor: Hiroyuki Omi, Kamakura (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 277 days.

(21) Appl. No.: 15/910,296

(22) Filed: Mar. 2, 2018

(65) Prior Publication Data
US 2018/0260966 A1 Sep. 13, 2018

(30) Foreign Application Priority Data
Mar. 8, 2017 (JP) .................................. 2017-044101

(51) Int. Cl.
  *G06T 7/32* (2017.01)
  *A61B 6/00* (2006.01)
  *G06T 5/00* (2006.01)

(52) U.S. Cl.
  CPC .............. *G06T 7/32* (2017.01); *A61B 6/4291* (2013.01); *A61B 6/5241* (2013.01); *A61B 6/5282* (2013.01); *G06T 5/001* (2013.01); *G06T 2200/32* (2013.01); *G06T 2207/10116* (2013.01); *G06T 2207/20221* (2013.01)

(58) Field of Classification Search
  CPC .................................................... A61B 6/5241
  See application file for complete search history.

(56) References Cited

U.S. PATENT DOCUMENTS

| | | | |
|---|---|---|---|
| 2016/0220202 A1* | 8/2016 | Tagawa | A61B 6/4266 |
| 2016/0220213 A1* | 8/2016 | Miyamoto | A61B 6/5252 |
| 2016/0249870 A1* | 9/2016 | Tajima | A61B 6/4291 378/62 |
| 2016/0270752 A1 | 9/2016 | Omi | |
| 2016/0354051 A1* | 12/2016 | Enomoto | A61B 6/5282 |

FOREIGN PATENT DOCUMENTS

JP 2015-192846 A 11/2015
JP 2016-131805 A 7/2016

* cited by examiner

*Primary Examiner* — Hoon K Song
(74) *Attorney, Agent, or Firm* — Carter, DeLuca & Farrell LLP

(57) ABSTRACT

Provided is a radiation imaging apparatus including: a radiation detector configured to generate a first radiographic image and a second radiographic image based on a radiation; a scattered radiation reduction unit configured to reduce a scattered radiation component from the first radiographic image and the second radiographic image; a position alignment unit configured to perform position alignment on the first radiographic image and the second radiographic image, using the first radiographic image and the second radiographic image from which the scattered radiation component has been reduced; and a combining unit configured to combine the first radiographic image and the second radiographic image that have been subjected to the position alignment.

17 Claims, 7 Drawing Sheets

RADIATION IMAGING APPARATUS, RADIATION IMAGING SYSTEM, RADIATION IMAGING METHOD, AND COMPUTER-READABLE MEDIUM THEREFOR

BACKGROUND OF THE INVENTION

Field of the Invention

The present invention relates to a radiation imaging apparatus, a radiation imaging system, a radiation imaging method, and a computer-readable medium therefor.

Description of the Related Art

During imaging using a radiation, two components of radiation are generated. The two components include a primary radiation transmitted straight ahead through an object (for example, human body) and a scattered radiation (secondary radiation) being a radiation scattered by a structure of the object (for example, human body structure). The scattered radiation is superimposed on a radiographic image as a component exhibiting an extremely low frequency within the radiographic image of the object, which lowers a contrast of the entire radiographic image, thereby lowering a diagnostic capability.

In order to prevent the above-mentioned lowering, a slit-shaped grating called "grid" is provided between the object and a radiation detection apparatus (radiation sensor). The scattered radiation that does not enter straight ahead from a radiation generation apparatus configured to generate a radiation is blocked by the grid before reaching the radiation detection apparatus, to thereby reduce the amount of scattered radiation entering the radiation detection apparatus. In general, the grid is designed to have such a focus as to transmit the primary radiation spreading in a cone shape, and is required to be used with a correct focal length and arrangement.

In medical practice, long-length imaging is sometimes performed by using an entire spine (entire backbone), a total length of a lower limb (entire leg), or other such long-length region as an object of radiation imaging. In the long-length imaging, an image of the long-length region exceeding an imaging region of one radiation detection apparatus is acquired. Therefore, in the case of performing the long-length imaging, the imaging region is enlarged by arranging a plurality of radiation detection apparatuses side by side, to thereby acquire the image of the long-length region by the plurality of radiation detection apparatuses.

After the long-length imaging, radiographic images obtained from the respective radiation detection apparatus are subjected to position alignment and combined, to thereby be able to obtain a long-length radiographic image including the entire object.

In related-art long-length imaging, the grid is used to suppress the scattered radiation. A grid for the long-length imaging using the plurality of radiation detection apparatuses arranged side by side is an extremely large and heavy grid, and is difficult to handle. In addition, in the long-length imaging, an imaging distance is different from an imaging distance used in normal imaging, which inhibits the same grid from being used to perform the long-length imaging and the normal imaging. When a grid optimized for one of the two kinds of imaging is used for the other kind of imaging, an insufficient dose or shading occurs, which causes deterioration in image quality and re-imaging.

Therefore, as in Japanese Patent Application Laid-Open No. 2016-131805 and Japanese Patent Application Laid-Open No. 2015-192846, there are disclosed scattered radiation estimation technologies for estimating and correcting a scattered radiation in a simple radiographic image without using a grid.

In such a case of simple radiography as in Japanese Patent Application Laid-Open No. 2016-131805 and Japanese Patent Application Laid-Open No. 2015-192846, a limited region of a body part is to be imaged, which allows a scattering state of the scattered radiation to be estimated from a structure of the body part to be imaged. The scattering state is expressed by a kernel for scattered radiation estimation. Through use of the kernel for scattered radiation estimation, it is possible to estimate an appropriate scattered radiation corresponding to the body part.

In the case of the long-length imaging using a plurality of radiation detection apparatuses arranged side by side, a region of one of the radiation detection apparatus is entered by a scattered radiation included in the region of the adjacent radiation detection apparatus, which necessitates a consideration of an influence of the scattered radiation. In order to take into consideration the influence of the scattered radiation that has entered from the adjacent radiation detection apparatus, it is required to calculate how the plurality of radiation detection apparatuses are arranged before performing the position alignment. However, it is difficult to perform the position alignment on the radiographic image entered by the scattered radiation, which leads to a problem in that accuracy in position alignment is low.

SUMMARY OF THE INVENTION

The present invention provides a radiation imaging apparatus capable of improving accuracy in position alignment exhibited when a plurality of radiographic images are combined.

According to one embodiment of the present invention, there is provided a radiation imaging apparatus including: a radiation detector configured to generate a first radiographic image and a second radiographic image based on a radiation; a scattered radiation reduction unit configured to reduce a scattered radiation component from the first radiographic image and the second radiographic image; a position alignment unit configured to perform position alignment on the first radiographic image and the second radiographic image, using the first radiographic image and the second radiographic image from which the scattered radiation component has been reduced; and a combining unit configured to combine the first radiographic image and the second radiographic image that have been subjected to the position alignment.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Figure 1:
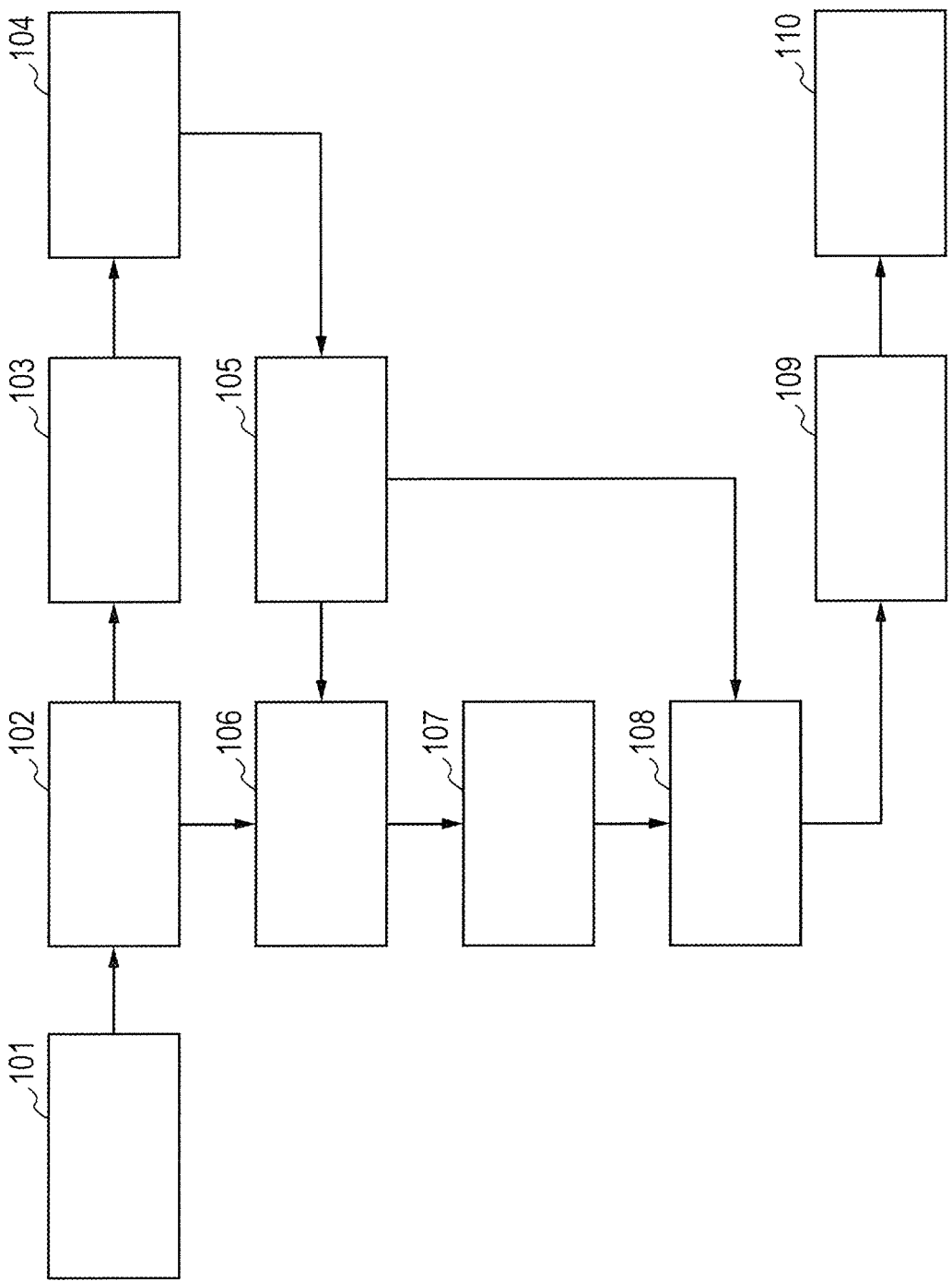
FIG. 1 is a diagram for illustrating a configuration example of a radiation imaging apparatus according to one embodiment of the present invention.

FIG. 1 is an illustration of a configuration example of a radiation imaging apparatus according to one embodiment of the present invention. The radiation imaging apparatus includes an image acquisition unit 101, a pre-processing unit 102, a first scattered radiation estimation unit 103, a first scattered radiation reduction unit 104, a position alignment unit 105, a second scattered radiation estimation unit 106, a second scattered radiation reduction unit 107, a combining unit 108, a post-processing unit 109, and an image output unit 110.

The image acquisition unit 101 receives input of a radiation transmitted through an object, converts the radiation into an image, and outputs the image as a raw image. The pre-processing unit 102 receives input of the raw image, and generates and outputs a radiographic image (hereinafter referred to as "pre-processed radiographic image") subjected to predetermined pre-processing. The first scattered radiation estimation unit 103 receives input of the pre-processed radiographic image, estimates a first scattered radiation, and outputs a first scattered radiation image. The first scattered radiation reduction unit 104 receives input of the pre-processed radiographic image and the first scattered radiation image, performs scattered radiation reduction processing, and outputs a first scattered radiation reduction image.

The position alignment unit 105 receives input of a plurality of first scattered radiation reduction images, performs position alignment on the plurality of first scattered radiation reduction images, calculates a position alignment parameter, and outputs the position alignment parameter.

The second scattered radiation estimation unit 106 receives input of a plurality of pre-processed radiographic images and the position alignment parameter, estimates a second scattered radiation, and outputs a second scattered radiation image. The second scattered radiation reduction unit 107 receives input of the pre-processed radiographic image and the second scattered radiation image, performs scattered radiation reduction processing, and outputs a second scattered radiation reduction image.

The combining unit 108 receives input of a plurality of second scattered radiation reduction images and the position alignment parameter, combines the plurality of second scattered radiation reduction images as one long-length image, and outputs the long-length image. The post-processing unit 109 receives input of the long-length image, and generates and outputs a radiographic image (post-processed radiographic image) subjected to frequency processing, gradation processing, or the like. The image output unit 110 outputs the post-processed radiographic image to a monitor, a film output apparatus, a picture archiving and communication system (PACS), or other such output device.

Figure 2:
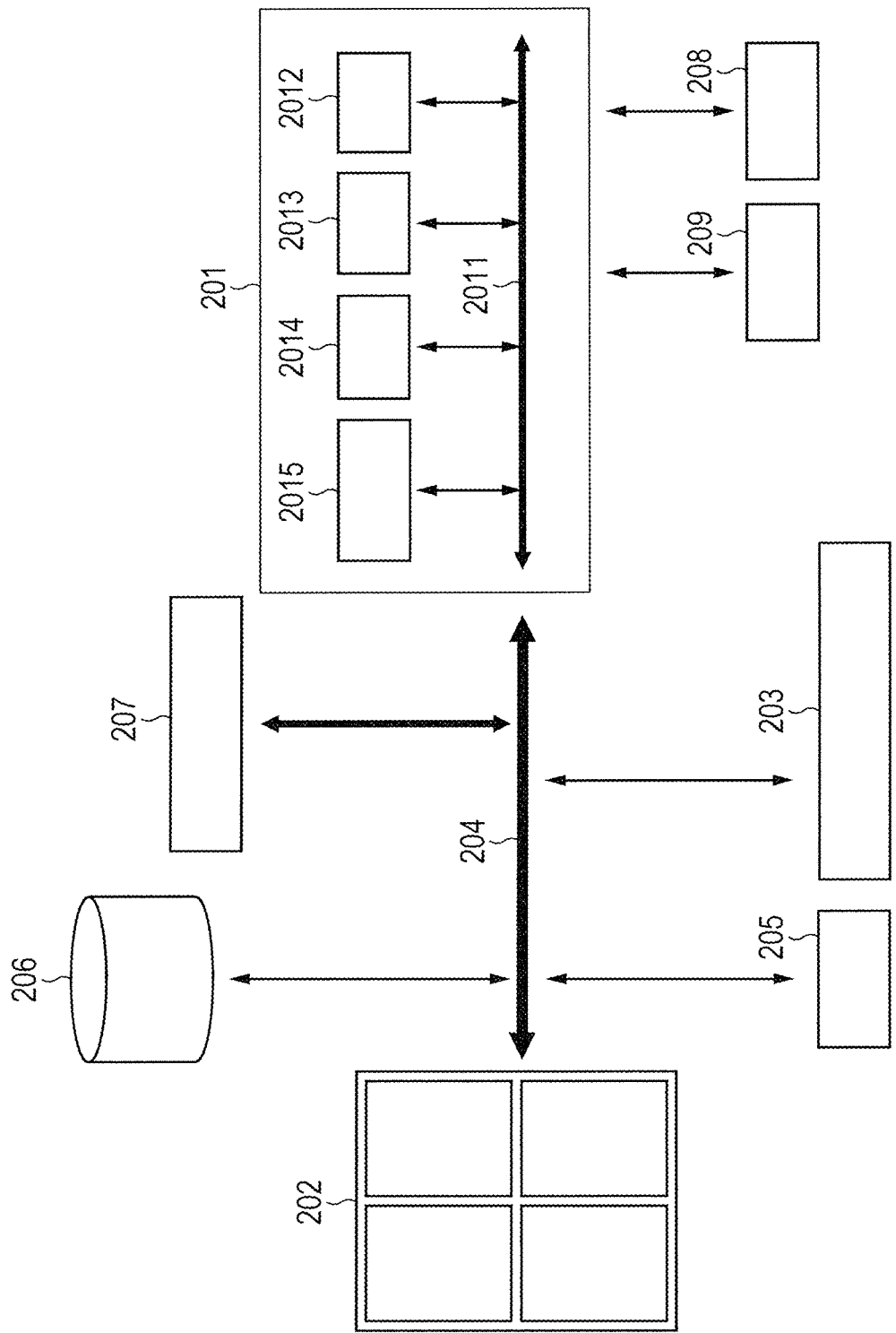
FIG. 2 is a diagram for illustrating a configuration example of a radiation imaging system including the radiation imaging apparatus according to the one embodiment.

FIG. 2 is a diagram for illustrating a configuration example of a radiation imaging system including the radiation imaging apparatus according to the one embodiment. A control PC 201, a radiation detection apparatus (a radiation detector) 202, and a radiation generation apparatus 203 are connected to a Gigabit Ethernet 204 serving as a signal line. In a case of long-length imaging using a plurality of radiation detection apparatuses 202, the plurality of radiation detection apparatuses 202 are connected to the Gigabit Ethernet 204. The signal line may be a controller area network (CAN), an optical fiber, or the like in place of the Gigabit Ethernet 204.

The Gigabit Ethernet 204 is connected to a display 205, a storage 206, and a network interface unit 207. The control PC 201 includes a central processing unit (CPU) 2012 connected to a bus 2011, a random-access memory (RAM) 2013, a read-only memory (ROM) 2014, and a storage 2015. The control PC 201 is connected to an input unit 208 via USB or PS/2, and connected to a display 209 via VGA or DVI. A command is transmitted to each of the radiation detection apparatus 202, the display 205, and the like via the control PC 201.

In the control PC 201, a processing procedure for each imaging mode is stored in the storage 2015 as a software module, and read into the RAM 2013 to be executed by the instruction means (not shown). The image acquisition unit 101 of FIG. 1 corresponds to the radiation detection apparatus 202. The pre-processing unit 102, the first scattered radiation estimation unit 103, the first scattered radiation reduction unit 104, the position alignment unit 105, the second scattered radiation estimation unit 106, the second scattered radiation reduction unit 107, the combining unit 108, and the post-processing unit 109 are stored in the storage 2015 as software modules.

The pre-processing unit 102, the first scattered radiation estimation unit 103, the first scattered radiation reduction unit 104, the position alignment unit 105, the second scattered radiation estimation unit 106, the second scattered radiation reduction unit 107, the combining unit 108, and the post-processing unit 109, which are illustrated in FIG. 1, may be implemented as a dedicated image processing board. Each of the processing units may be optimally implemented depending on the purpose.

The image output unit 110 of FIG. 1 corresponds to the display 205 or the storage 206, which is connected via the Gigabit Ethernet 204, or the display 209 connected to the control PC 201.

Operations performed by the above-mentioned radiation imaging apparatus or the above-mentioned radiation imaging system according to the one embodiment are described below in detail with reference to the following embodiments.

First Embodiment

Figure 3:
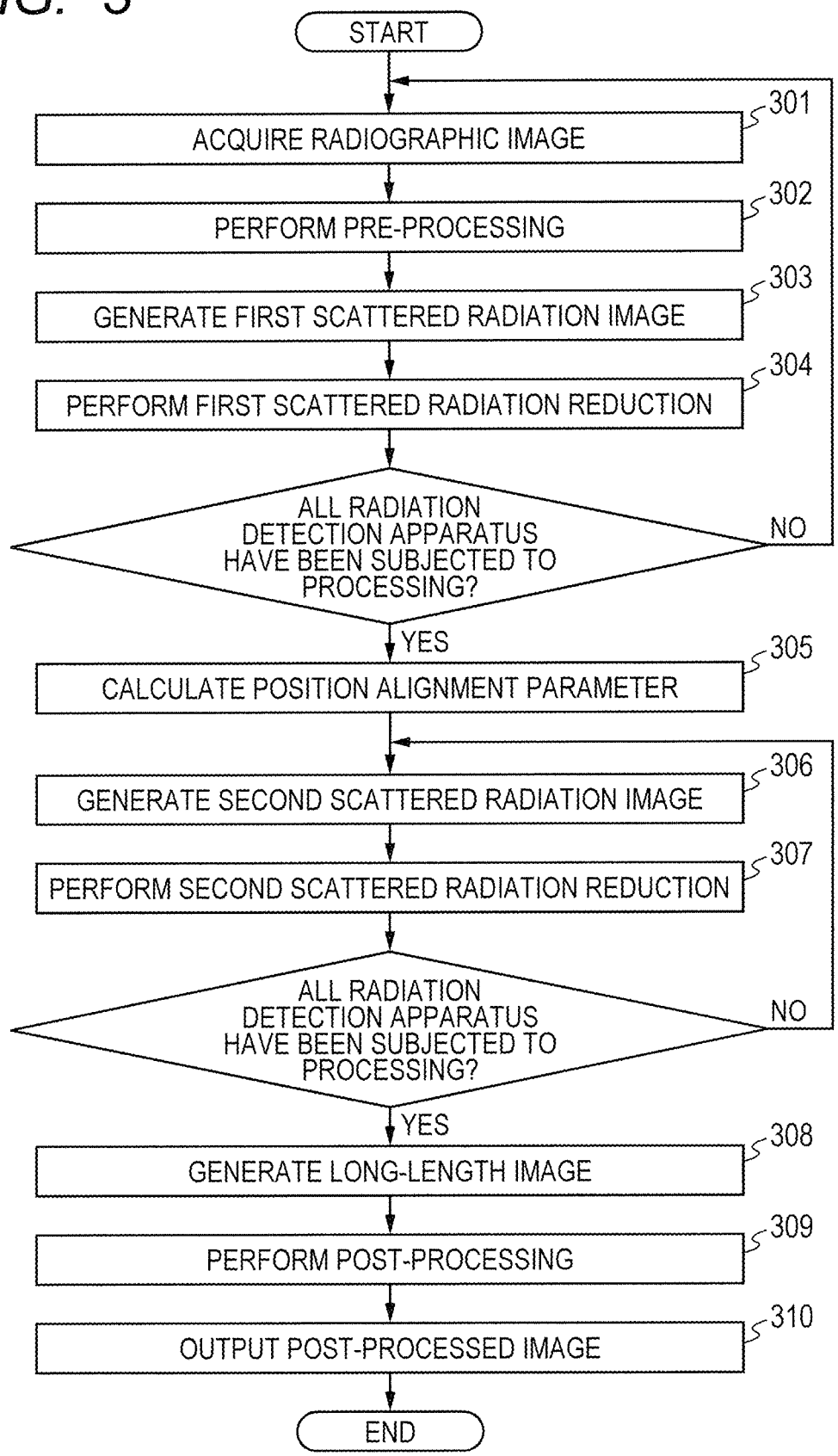
FIG. 3 is a flowchart for illustrating an example of an operation of a radiation imaging system according to a first embodiment of the present invention.

With reference to FIG. 1 and FIG. 3, a first embodiment of the present invention is described along the flow of processing. FIG. 3 is a flowchart for illustrating an example of an operation of a radiation imaging system according to the first embodiment.

The image acquisition unit 101 causes the radiation detection apparatus 202 to acquire an image, and performs an offset correction (dark current correction) on the acquired image to generate a raw image (Step 301). For example, in the case of long-length imaging using two radiation detection apparatus 202, two raw images are generated. The radiation detection apparatus 202 generates a first radiographic image and a second radiographic image based on a radiation.

Subsequently, the pre-processing unit 102 performs pre-processing on the raw image to generate a pre-processed radiographic image (Step 302). The pre-processing represents processing for correcting characteristics of a sensor of the radiation detection apparatus 202, and includes performing gain correction, loss correction, and the like to achieve a state under which correlations between a pixel value of a given pixel and pixel values of the peripheral pixels are maintained.

Subsequently, the first scattered radiation estimation unit 103 performs first scattered radiation estimation on each of the pre-processed radiographic images generated through use of the plurality of radiation detection apparatuses 202 to generate a first scattered radiation image (Step 303). The first scattered radiation estimation represents estimating a scattered radiation for each of the plurality of pre-processed radiographic images without taking the influence of another pre-processed radiographic image into consideration, and is therefore simple scattered radiation estimation.

Figure 4A:
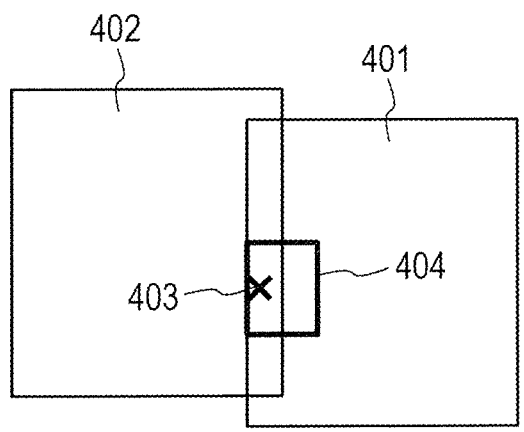
FIG. 4A is a schematic diagram for illustrating a region used for first scattered radiation estimation.

FIG. 4A is a schematic diagram for illustrating a region used for the first scattered radiation estimation. A pixel 403 at which a scattered radiation is to be estimated is positioned at an edge of an image obtained by a radiation detection apparatus 401, and positioned in a region overlapping with another imaging region adjacent thereto. In this case, in order to appropriately estimate the scattered radiation in an overlapping region, it is required to take into consideration the influence of a scattered radiation from a radiation detection apparatus 402 adjacent thereto, but in the first scattered radiation estimation, the influence of the scattered radiation from the radiation detection apparatus 402 is not taken into consideration.

In the first scattered radiation estimation, the scattered radiation at the pixel 403 is estimated from the pixel values of the pre-processed radiographic image for an estimation region 404 of the radiation detection apparatus 401 without taking into consideration the pixel values of the pre-processed radiographic image obtained by the radiation detection apparatus 402. The estimation region 404 is set in the pre-processed radiographic image obtained by the radiation detection apparatus 401. As a method for the scattered radiation estimation, such a known technology as disclosed in Japanese Patent Application Laid-Open No. 2016-131805, Japanese Patent Application Laid-Open No. 2015-192846, or the like can be employed.

Subsequently, the first scattered radiation reduction unit 104 performs first scattered radiation reduction (Step 304). The first scattered radiation reduction unit 104 removes the first scattered radiation image obtained in Step 303 from the pre-processed radiographic image, to thereby generate the first scattered radiation reduction image.

When the pre-processed radiographic image (formed of a set of pixel values) is represented by M and a first scattered radiation reduction image (formed of a set of pixel values) is represented by $P_1$, the first scattered radiation reduction image $P_1$ is calculated from "M" and a scattered radiation estimation function funcS being a mathematical function of "M".

For example, in the case of the long-length imaging using the radiation detection apparatus 401 and 402, the radiation detection apparatus 401 generates a pre-processed radiographic image (first radiographic image) $M_1$ based on a radiation, and the radiation detection apparatus 402 generates a pre-processed radiographic image (second radiographic image) $M_2$.

As expressed by Expression (1), a first scattered radiation reduction image $P_{11}$ for the radiation detection apparatus 401 is generated from the pre-processed radiographic image $M_1$ generated through use of the radiation detection apparatus 401 and a first scattered radiation image funcS($M_1$). Meanwhile, as expressed by Expression (2), a first scattered radiation reduction image $P_{12}$ for the radiation detection apparatus 402 is generated from the pre-processed radiographic image $M_2$ generated through use of the radiation detection apparatus 402 and the first scattered radiation image funcS($M_2$).

$$P_{11}(i,j)=M_1(i,j)-\text{funcS}(M_1) \qquad (1)$$

$$P_{12}(i,j)=M_2(i,j)-\text{funcS}(M_2) \qquad (2)$$

In this manner, the first scattered radiation reduction unit 104 performs first processing for reducing a scattered radiation component on the pre-processed radiographic image (first radiographic image) $M_1$ and the pre-processed radiographic image (second radiographic image) $M_2$ to generate the first scattered radiation reduction images $P_{11}$ and $P_{12}$.

In the first processing, a first scattered radiation component funcS($M_1$) of the first radiographic image $M_1$ is estimated based on the first radiographic image $M_1$, and the first scattered radiation component funcS($M_1$) is removed from the first radiographic image $M_1$, to thereby reduce the scattered radiation component from the first radiographic image. In addition, in the first processing, a second scattered radiation component funcS($M_2$) of the second radiographic image $M_2$ is estimated based on the second radiographic image $M_2$, and the second scattered radiation component funcS($M_2$) is removed from the second radiographic image $M_2$, to thereby reduce the scattered radiation component from the second radiographic image.

The first scattered radiation reduction images $P_{11}$ and $P_{12}$, in each of which the scattered radiation from the adjacent radiation detection apparatus is not taken into consideration, are not high in accuracy in scattered radiation estimation, and therefore have scattered radiation components remaining therein. However, a certain amount of low-frequency components can be removed, thereby increasing the contrast of the entire image compared to the pre-processed radiographic image.

After the first scattered radiation reduction unit 104 generates the first scattered radiation reduction image $P_1$, the control PC 201 determines whether or not the processing has been performed on the radiographic images obtained from all the radiation detection apparatus. When there is a radiographic image from a radiation detection apparatus that has not been subjected to the processing, the control PC 201 returns the processing to Step 301. When determining that the processing has been performed on the radiographic images obtained from all the radiation detection apparatus, the control PC 201 advances the processing to Step 305.

Subsequently, the position alignment unit 105 uses the first scattered radiation reduction images $P_{11}$ and $P_{12}$ to calculate a position alignment parameter (Step 305). Positional information on the radiation detection apparatus 202 can be obtained from a hardware device, for example, a position sensor built in a standing posture imaging base or a table for external imaging that contains the radiation detection apparatus 202 or a position sensor built in the radiation detection apparatus 202. The positional information can also be used as the position alignment parameter. That is, the position alignment unit 105 may perform the position alignment based on the positions of the radiation detection apparatus 401 and 402 measured by the position sensors.

However, there may occur a difference in positional information between a timing to acquire the position alignment parameter and a timing to acquire the radiographic image. To handle this, the positional information may also be acquired from the radiographic image. In this case, in order to calculate the positional information, image matching processing is performed. In the case of performing the long-length imaging, the plurality of radiation detection apparatuses 202 are arranged so as to have an overlap in a part of a plurality of adjacent imaging regions.

The matching processing is performed through use of the overlapping region of the plurality of imaging regions. A part of the overlapping region of one imaging region is used as a template, and the template is shifted in position to calculate a similarity S with the overlapping region (input image) of another imaging region. For example, the similarity S is calculated through use of such a normal cross-correlation as expressed by Expression (3).

$$S = \frac{\sum\sum \{g(d_x + i, d_y + j) f(i, j)\}}{\sqrt{\sum\sum (g(d_x + i, d_y + j))^2} \sqrt{\sum\sum (f(i, j))^2}} \quad (3)$$

In Expression (3), $f(i,j)$ represents a template image formed of the pixel value of the one radiographic image at $(i,j)$, and $g(d_x, d_y)$ represents an input image formed of the pixel value of the another radiographic image at a shift amount $(d_x, d_y)$ of the template image. The position alignment unit 105 calculates, as the positional information, $(d_x, d_y)$ obtained when the similarity S becomes maximum. The position alignment unit 105 outputs the output calculated positional information as the position alignment parameter.

In Expression (3), a shift amount is used as the position alignment parameter, but a rotation angle of the template image may be added to the position alignment parameter.

In this manner, the position alignment unit 105 uses the first radiographic image subjected to the first processing and the second radiographic image subjected to the first processing to perform the position alignment on the first radiographic image and the second radiographic image, to thereby output the position alignment parameter. The position alignment unit 105 performs the position alignment so that the images of the overlapping region corresponding to an overlap between the imaging regions of the first radiographic image and the second radiographic image match each other.

Subsequently, the second scattered radiation estimation unit 106 performs second scattered radiation estimation on each of the pre-processed radiographic images generated through use of the plurality of radiation detection apparatuses 202 to generate a second scattered radiation image (Step 306). The second scattered radiation estimation represents estimating a scattered radiation for each of the plurality of pre-processed radiographic images by taking the influence of another pre-processed radiographic image into consideration, and is therefore detailed scattered radiation estimation.

Figure 4B:
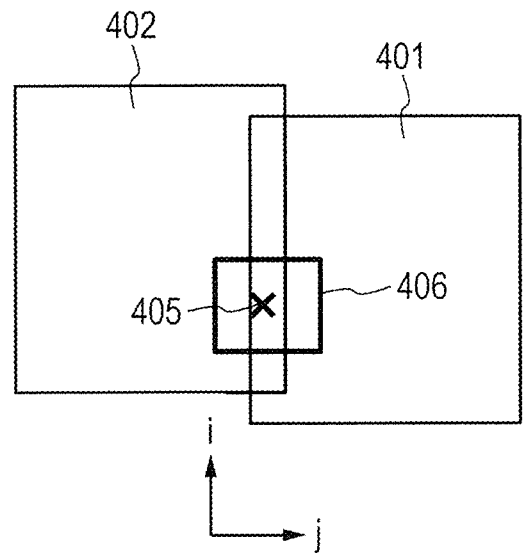
FIG. 4B is a schematic diagram for illustrating a region used for second scattered radiation estimation.

FIG. 4B is a schematic diagram for illustrating a region used for the second scattered radiation estimation. A pixel 405 at which a scattered radiation is to be estimated is positioned at an edge of an image obtained by the radiation detection apparatus 401, and positioned in a region overlapping with another imaging region adjacent thereto. In this case, in order to appropriately estimate the scattered radiation in an overlapping region, it is required to take into consideration the influence of a scattered radiation from the radiation detection apparatus 402 adjacent thereto, and thus in the second scattered radiation estimation, the influence of the scattered radiation from the radiation detection apparatus 402 is taken into consideration.

In the second scattered radiation estimation, the scattered radiation at the pixel 405 is estimated from the pixel values of the pre-processed radiographic image for an estimation region 406 of the radiation detection apparatus 401 and the radiation detection apparatus 402 by taking into consideration the pixel values of the pre-processed radiographic image obtained by the radiation detection apparatus 402. The estimation region 406 is set in the pre-processed radiographic image obtained by the radiation detection apparatus 401 and the radiation detection apparatus 402. As a method for the scattered radiation estimation, such a known technology as disclosed in Japanese Patent Application Laid-Open No. 2016-131805, Japanese Patent Application Laid-Open No. 2015-192846, or the like can be employed.

In this manner, when the pixel 405 at which the scattered radiation is to be estimated is located at the edge of the image, the estimation region 406 is set to the region including not only the radiation detection apparatus 401 but also the radiation detection apparatus 402. When the estimation region 406 is set in a part of the radiation detection apparatus 402, the position alignment needs to be performed on the pre-processed radiographic images generated through use of the radiation detection apparatus 401 and the radiation detection apparatus 402. The position alignment parameter calculated in Step 305 is used for the position alignment.

When the position alignment is appropriately performed on the pre-processed radiographic images generated through use of the radiation detection apparatus 401 and the radiation detection apparatus 402, a region that exerts an influence on the scattered radiation estimation at the pixel 405 is accurately obtained. As a result, the accuracy in scattered radiation estimation is improved.

Subsequently, the second scattered radiation reduction unit 107 performs second scattered radiation reduction (Step 307). The second scattered radiation reduction unit 107 removes the second scattered radiation image obtained in Step 306 from the pre-processed radiographic image, to thereby generate the second scattered radiation reduction image.

When the pre-processed radiographic image is represented by M and the second scattered radiation reduction image is represented by $P_2$, the second scattered radiation reduction image $P_2$ is calculated from M and the scattered radiation estimation function funcS being a mathematical function of M.

For example, in the case of the long-length imaging using the radiation detection apparatus 401 and 402, a second scattered radiation reduction image $P_{21}$ for the radiation detection apparatus 401 is generated from the pre-processed radiographic image $M_1$ generated through use of the radiation detection apparatus 401 and a second scattered radiation image $funcS(M_1, M_2)$ as expressed by Expression (4). Meanwhile, a second scattered radiation reduction image $P_{22}$ for the radiation detection apparatus 402 is generated from the pre-processed radiographic image $M_2$ generated through use of the radiation detection apparatus 402 and the second scattered radiation image $funcS(M_1, M_2)$ as expressed by Expression (5).

$$P_{21}(i,j) = M_1(i,j) - funcS(M_1, M_2) \quad (4)$$

$$P_{22}(i,j) = M_2(i,j) - funcS(M_1, M_2) \quad (5)$$

In this manner, the second scattered radiation estimation unit 106 estimates the scattered radiation component $funcS(M_1, M_2)$ of the first radiographic image $M_1$ and the second radiographic image $M_2$ based on the first radiographic image $M_1$ and the second radiographic image $M_2$ that have been subjected to the position alignment. Then, the second scattered radiation reduction unit 107 performs second processing for removing the estimated scattered radiation component $funcS(M_1, M_2)$ from the first radiographic image $M_1$ and the second radiographic image $M_2$.

In the second processing, a second scattered radiation component $funcS(M_1, M_2)$ of the first radiographic image $M_1$ is estimated based on the first radiographic image $M_1$ and the second radiographic image $M_2$ that have been subjected to the position alignment. Then, the second scattered radiation component $funcS(M_1, M_2)$ is removed from the first radiographic image $M_1$, to thereby reduce the scattered radiation component from the first radiographic image $M_1$.

Meanwhile, in the second processing, the second scattered radiation component $funcS(M_1, M_2)$ of the second radiographic image $M_2$ is estimated based on the first radiographic image $M_1$ and the second radiographic image $M_2$ that have been subjected to the position alignment. Then, the second scattered radiation component $funcS(M_1, M_2)$ is removed from the second radiographic image $M_2$, to thereby reduce the scattered radiation component from the second radiographic image $M_2$. With those processing steps, the second scattered radiation reduction unit 107 generates the second scattered radiation reduction images.

The second scattered radiation reduction images, in which the scattered radiation from the adjacent radiation detection apparatus is taken into consideration, are high in accuracy in scattered radiation estimation, and therefore have an increased contrast of the entire image compared to the first scattered radiation reduction images $P_{11}$ and $P_{12}$ generated in Step 304.

After the second scattered radiation reduction unit 107 generates the second scattered radiation reduction image, the control PC 201 determines whether or not the processing has been performed on the radiographic images obtained from all the radiation detection apparatus 202. When there is a radiographic image from a radiation detection apparatus 202 that has not been subjected to the processing, the control PC 201 returns the processing to Step 306. When determining that the processing has been performed on the radiographic images obtained from all the radiation detection apparatus 202, the control PC 201 advances the processing to Step 308.

Subsequently, the combining unit 108 combines the plurality of second scattered radiation reduction images to generate a long-length image (Step 308). The combining unit 108 combines the first radiographic image and the second radiographic image that have been subjected to the second processing at the positions of the first radiographic image and the second radiographic image that have been subjected to the position alignment.

For example, in the case of the long-length imaging using the two radiation detection apparatus 401 and 402, one long-length image is generated from two second scattered radiation reduction images. In order to generate the long-length image, the combining unit 108 uses the position alignment parameter calculated in Step 305 to perform the position alignment on the plurality of second scattered radiation reduction images. Then, combining processing is performed on the second scattered radiation reduction images that have been brought into a correct positional relationship.

In the first embodiment, the combining unit 108 combines the first radiographic image and the second radiographic image that have been subjected to the second processing through weighting based on a distance from a predetermined coordinate in a coordinate system of the first radiographic image and the second radiographic image that have been subjected to the position alignment. The combining processing is performed through blending processing involving the weighting based on the position of the overlapping region as expressed by, for example, Expression (6). In this case, the predetermined coordinate in the coordinate system is a center cy of the overlapping region corresponding to the overlap between the imaging regions of the first radiographic image and the second radiographic image.

$$P_c(i,j) = (1 - w(cy - j)) \cdot P_{21}(i,j) + w(cy - j) \cdot P_{22}(i,j) \quad (6)$$

A combined image $P_c(i,j)$ is obtained by combining a second scattered radiation reduction image $P_{21}(i,j)$ for the radiation detection apparatus 401 and a second scattered radiation reduction image $P_{22}(i,j)$ for the radiation detection apparatus 402 through the weighting. The combination through the weighting is performed through use of a weighting factor $w(cy-j)$ being a mathematical function of a distance $(cy-j)$ from the center cy (center cy of gravity) of the overlapping region between the imaging regions of the radiation detection apparatus 401 and 402.

In this case, i represents a coordinate in a direction perpendicular to a direction (arrangement direction) in which the radiation detection apparatus 401 and 402 are arranged, and j represents a coordinate in a direction parallel to the direction in which the radiation detection apparatus 401 and 402 are arranged.

Further, cy represents a j-axis coordinate of the position of the center of the overlapping region. The j-axis may be a short-side direction of the overlapping region. The j-axis may also be a direction parallel to a straight line that connects the centers (centers of gravity) of the imaging regions of the radiation detection apparatus 401 and 402. That is, the distance from the center cy of gravity is the distance in the direction parallel to at least one of the arrangement direction of the first radiographic image and the second radiographic image, the short-side direction of the overlapping region, or the direction of the straight line that connects the centers of the first radiographic image and the second radiographic image.

An image of an edge part of the radiation detection apparatus is included in the overlapping region between the imaging regions of the radiation detection apparatus 401 and 402 adjacent to each other, and hence an image of a sensor structure of the radiation detection apparatus 401 or 402 may be included in the obtained image. In such a case, for example, data relating to the sensor structure is acquired in advance, and at the above-mentioned timing, processing for removing the included image of the sensor structure is performed.

The post-processing unit 109 performs post-processing on the long-length image to generate a post-processed radiographic image (Step 309). The post-processing represents processing for generating an image optimal for diagnosis, and includes frequency processing or gradation processing.

Finally, the image output unit 110 outputs a post-processed image to a display device (Step 310). Examples of the display device include a monitor, a film output device, and a PACS.

In this manner, after the first scattered radiation estimation is performed, the position alignment is performed on the plurality of radiation detection apparatuses through use of the first scattered radiation reduction images $P_{11}$ and $P_{12}$. A result of the position alignment is used to perform second scattered radiation estimation, to thereby allow the scattered radiation estimation to be performed based on a highly-accurate position alignment parameter. Therefore, the accuracy in scattered radiation estimation for the long-length image is improved to achieve higher image quality of the long-length image subjected to the scattered radiation reduction processing.

In the first embodiment, the simple scattered radiation estimation that does not take the influence of another pre-processed radiographic image into consideration is performed as the first scattered radiation estimation of Step 303, but the first scattered radiation estimation may be detailed scattered radiation estimation that takes the influence of another pre-processed radiographic image into consideration.

In this case, as described above, the position alignment unit 105 performs the position alignment on the radiographic images generated through use of the plurality of radiation detection apparatuses 401 and 402 based on the position alignment parameter obtained from the position sensor or other such hardware device. The position alignment unit 105 uses the first radiographic image subjected to the first processing and the second radiographic image subjected to the first processing to perform the position alignment on the first radiographic image and the second radiographic image, to thereby output the position alignment parameter.

Figure 4C:
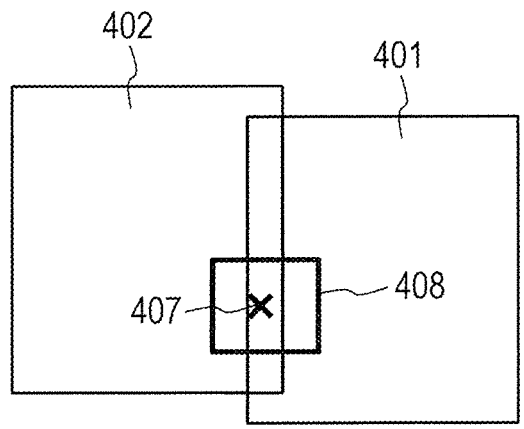
FIG. 4C is a schematic diagram for illustrating a modification example of the region used for the first scattered radiation estimation.

Then, as illustrated in FIG. 4C, a scattered radiation at a pixel 407 is estimated from the pixel values of an estimation region 408 set in the pre-processed radiographic images obtained by the radiation detection apparatus 401 and the radiation detection apparatus 402.

Therefore, the first scattered radiation reduction image $P_{11}$ for the radiation detection apparatus 401 is generated from the pre-processed radiographic image $M_1$ generated through use of the radiation detection apparatus 401 and the pre-processed radiographic image $M_2$ generated through use of the radiation detection apparatus 402 as expressed by Expression (7). Meanwhile, the first scattered radiation reduction image $P_{12}$ for the radiation detection apparatus 402 is generated from the pre-processed radiographic image $M_1$ generated through use of the radiation detection apparatus 401 and the pre-processed radiographic image $M_2$ generated through use of the radiation detection apparatus 402 as expressed by Expression (8).

$$P_{11}(i,j)=M_1(i,j)-\text{func}S(M_1,M_2) \quad (7)$$

$$P_{12}(i,j)=M_2(i,j)-\text{func}S(M_1,M_2) \quad (8)$$

In this manner, the first scattered radiation estimation unit 103 estimates the scattered radiation component funcS($M_1$, $M_2$) of the first radiographic image $M_1$ and the second radiographic image $M_2$ based on the first radiographic image $M_1$ and the second radiographic image $M_2$ that have been subjected to the position alignment. Then, the first scattered radiation reduction unit 104 performs first processing for removing the estimated scattered radiation component funcS($M_1$,$M_2$) from the first radiographic image $M_1$ and the second radiographic image $M_2$.

In the first processing, a first scattered radiation component funcS($M_1$,$M_2$) of the first radiographic image $M_1$ is estimated based on the first radiographic image $M_1$ and the second radiographic image $M_2$ that have been subjected to the position alignment. Then, the first scattered radiation component funcS($M_1$,$M_2$) is removed from the first radiographic image $M_1$, to thereby reduce the scattered radiation component from the first radiographic image $M_1$.

Meanwhile, in the first processing, the first scattered radiation component funcS($M_1$,$M_2$) of the second radiographic image $M_2$ is estimated based on the first radiographic image $M_1$ and the second radiographic image $M_2$ that have been subjected to the position alignment. Then, the first scattered radiation component funcS($M_1$,$M_2$) is removed from the second radiographic image $M_2$, to thereby reduce the scattered radiation component from the second radiographic image $M_2$.

Further, in the first embodiment, after the second scattered radiation reduction images are each generated in Step 307, the second scattered radiation reduction images are combined in Step 308, to thereby generate the long-length image. However, the second scattered radiation reduction image for a long-length image may be generated after the long-length image is obtained through the combination. In this case, the combining unit 108 combines the first radiographic image and the second radiographic image that have been subjected to the first processing at the positions of the first radiographic image and the second radiographic image that have been subjected to the position alignment. After the long-length image is obtained through the combination, the second scattered radiation image is generated to generate the second scattered radiation reduction image in the same manner as described above.

Further, in the first embodiment, the first processing is performed on the first radiographic image and the second radiographic image, but it suffices that the first processing is performed on at least one of the first radiographic image or the second radiographic image. For example, when the first processing is performed on the first radiographic image, the first scattered radiation reduction unit 104 performs the first processing for reducing the scattered radiation component from the first radiographic image.

The position alignment unit 105 uses the first radiographic image subjected to the first processing to perform the position alignment on the first radiographic image and the second radiographic image. The second scattered radiation estimation unit 106 uses the positional relationship between the first radiographic image and the second radiographic image that have been subjected to the position alignment to estimate the scattered radiation component of the radiographic image of at least one of the first radiographic image or the second radiographic image based on the first radiographic image and the second radiographic image that have been subjected to the position alignment. The second scattered radiation reduction unit 107 performs the second processing for removing the estimated scattered radiation component from the radiographic image of at least one of the first radiographic image or the second radiographic image.

Second Embodiment

An example of a second embodiment of the present invention is described in detail. Descriptions of the same configurations, functions, and operations as those of the above-mentioned embodiment are omitted, and different points from those of the first embodiment are mainly described.

In the first embodiment, the second scattered radiation estimation is performed separately from the first scattered radiation estimation, but may be performed through use of the first scattered radiation images funcS($M_1$) and funcS ($M_2$) obtained as a result of the first scattered radiation estimation.

The pixel of the radiation detection apparatus 401 influenced by the scattered radiation from the adjacent radiation detection apparatus 402 is the pixel 403 close to the adjacent radiation detection apparatus 402. Therefore, a pixel of the radiation detection apparatus 401 (or first radiographic image) far from the adjacent radiation detection apparatus 402 (or second radiographic image) is hardly influenced by the scattered radiation from the adjacent radiation detection apparatus 402 (or second radiographic image). As a result, the first scattered radiation image calculated in Step 303 is used to perform second scattered radiation reduction in Step 307.

In this manner, the second scattered radiation reduction unit 107 removes a first scattered radiation component estimated based on the first radiographic image from the first radiographic image at a position that exceeds a predetermined range from the position of the second radiographic image subjected to the position alignment.

Meanwhile, the second scattered radiation reduction unit 107 removes a second scattered radiation component estimated based on the first radiographic image and the second radiographic image that have been subjected to the position alignment from the first radiographic image at a position within the predetermined range from the position of the second radiographic image subjected to the position alignment, to thereby perform the second processing.

The second scattered radiation reduction unit 107 removes the first scattered radiation component estimated based on the first radiographic image from the first radiographic image at a position that exceeds a predetermined range from the overlapping region corresponding to the overlap between the imaging regions of the first radiographic image and the second radiographic image that have been subjected to the position alignment. Meanwhile, the second scattered radiation reduction unit 107 removes the second scattered radiation component estimated based on the first radiographic image and the second radiographic image that have been subjected to the position alignment from the first radiographic image at a position within the predetermined range from the overlapping region.

Figure 4D:
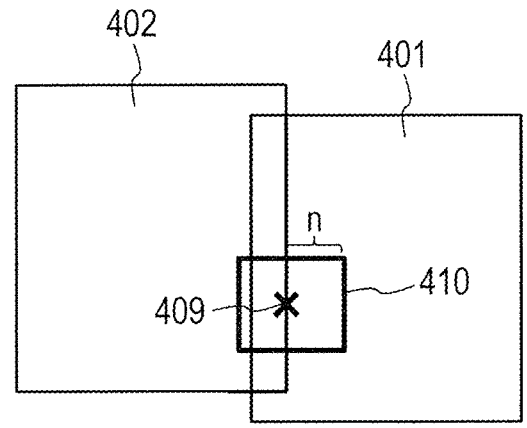
FIG. 4D is a schematic diagram for illustrating a modification example of the region used for the second scattered radiation estimation.

As illustrated in FIG. 4D, when a region including (n+1) pixels from a pixel 409 at which the scattered radiation is to be estimated up to an n-th pixel in a j-axis direction needs to be set as an estimation region 410, the region influenced by the radiation detection apparatus 402 falls within a range of n pixels from the edge of the overlapping region in the j-axis direction. At a pixel that exceeds the range of n pixels from the edge of the overlapping region in the j-axis direction, the influence exerted by the radiation detection apparatus 402 is not taken into consideration in the second scattered radiation estimation. That is, $M_2$ becomes 0 in Expression (4) and Expression (5), and Expression (4) and Expression (5) become equal to Expression (1) and Expression (2), respectively.

Therefore, the result of the first scattered radiation estimation can be used as it is, and hence the second scattered radiation reduction unit 107 removes the first scattered radiation image obtained in Step 303 from the pre-processed radiographic image, to thereby generate the second scattered radiation reduction image.

In this manner, the second scattered radiation reduction unit 107 generates the second scattered radiation image in the range in which the influence exerted by the adjacent radiation detection apparatus 402 is to be taken into consideration, and in the other range, uses the first scattered radiation image to generate the second scattered radiation reduction image. There is a limit to the range in which the second scattered radiation estimation is to be performed, which can suppress a calculation cost required for generating the second scattered radiation reduction image.

Third Embodiment

An example of a third embodiment of the present invention is described in detail. Descriptions of the same configurations, functions, and operations as those of the above-mentioned embodiments are omitted, and different points from those of the above-mentioned embodiments are mainly described.

Figure 5:
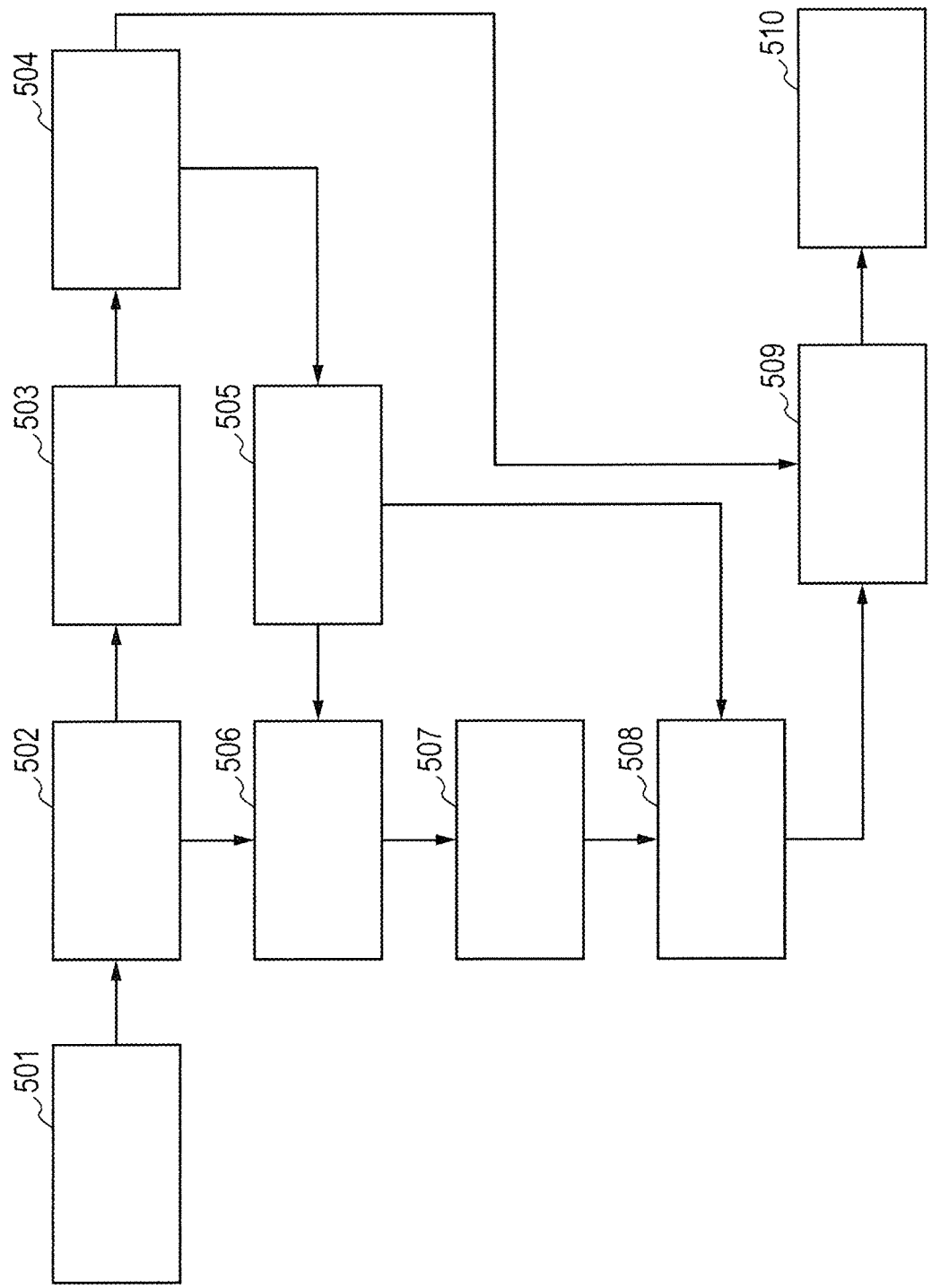
FIG. 5 is a diagram for illustrating a configuration example of a radiation imaging system including a radiation imaging apparatus according to a third embodiment of the present invention.
Figure 6:
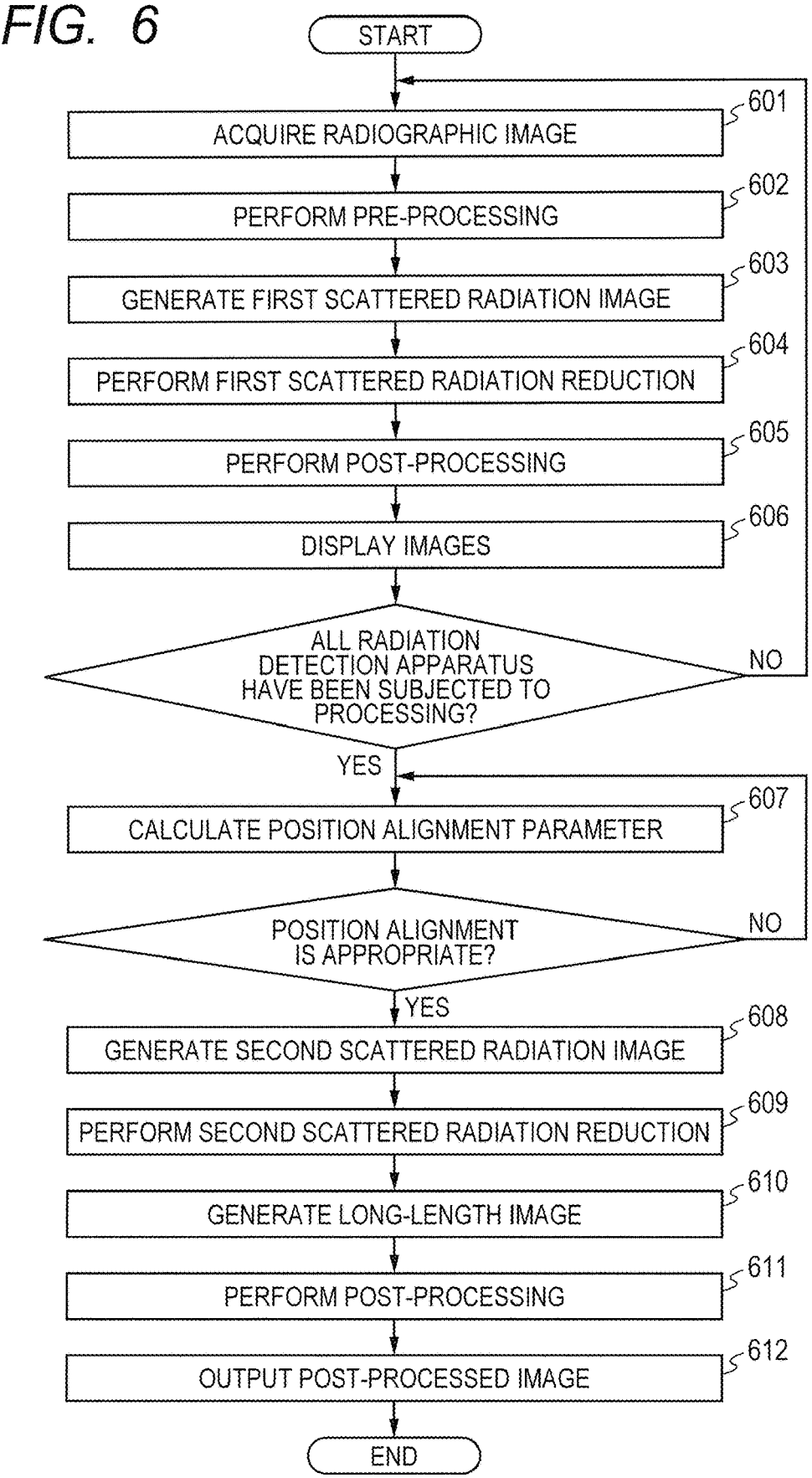
FIG. 6 is a flowchart for illustrating an example of an operation of a radiation imaging system according to the third embodiment.

An embodiment for separately performing the first scattered radiation estimation and the second scattered radiation estimation is described along the flow of processing with reference to a configuration diagram of FIG. 5 and a flowchart of FIG. 6.

Components 501 to 510 of FIG. 5 correspond to the components 101 to 110 of FIG. 1, respectively. Step 601 to Step 604 correspond to Step 301 to Step 304 of the first embodiment, respectively. Hence, descriptions thereof are omitted.

The post-processing unit 509 performs the post-processing on a plurality of first scattered radiation reduction images $P_{11}$ and $P_{12}$ to generate a plurality of post-processed first scattered radiation reduction images (Step 605).

Subsequently, the image output unit 510 displays the plurality of post-processed first scattered radiation reduction images on a monitor (Step 606). That is, the first radiographic image subjected to the first processing and the second radiographic image subjected to the first processing are displayed on a display (monitor).

Figure 7:
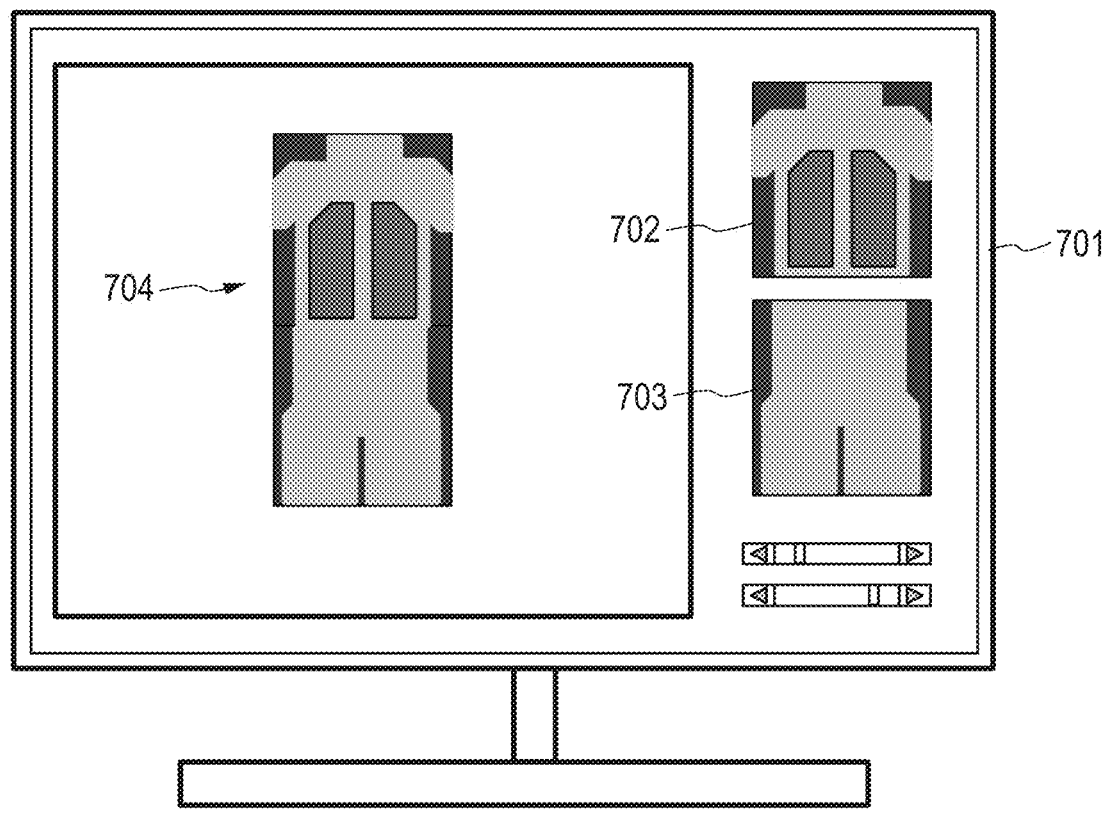
FIG. 7 is a diagram for illustrating a display example of a plurality of post-processed first scattered radiation reduction images obtained in long-length imaging using a radiation detection apparatus.

FIG. 7 is an illustration of a display example of the plurality of post-processed first scattered radiation reduction images that are obtained in the long-length imaging using the radiation detection apparatus 401 and 402. In FIG. 7, a post-processed first scattered radiation reduction image 702 for the radiation detection apparatus 401 and a post-processed first scattered radiation reduction image 703 for the radiation detection apparatus 402 are displayed as two images displayed on a monitor 701.

The post-processed first scattered radiation reduction image 702 and the post-processed first scattered radiation reduction image 703 are displayed for the purpose of verifying whether or not the imaging has been appropriately performed, whether or not there is an imaging failure, and the like. In verification work, it is possible to correctly perform determination by displaying the post-processed first scattered radiation reduction images 702 and 703 that have accuracy close to that of a diagnostic image output at a final stage.

In the third embodiment, the simple scattered radiation estimation that does not take the influence of another pre-processed radiographic image into consideration is performed (Step 603), to thereby be able to generate the first scattered radiation reduction image having a reduced amount of scattered radiation without the need to perform the position alignment with the adjacent radiation detection apparatus (Step 604). Then, the post-processing is performed on the first scattered radiation reduction image, to thereby be able to determine whether or not the imaging has been appropriately performed and whether or not there is an imaging failure based on a radiographic image having high image quality. In addition, there is no need to perform the position alignment with the adjacent radiation detection apparatus, and hence the calculation cost is suppressed, while the post-processed first scattered radiation reduction images are displayed at an early stage, to thereby be able to shorten a time period required before starting the verification work.

The control PC 201 determines whether or not the post-processed first scattered radiation reduction images have been displayed for all the radiation detection apparatus. When there is a radiation detection apparatus that has not been subjected to the processing, the control PC 201 returns the processing to Step 601. When determining that the post-processed first scattered radiation reduction images have been displayed for all the radiation detection apparatus, the control PC 201 advances the processing to Step 607.

When the imaging has been appropriately performed and there has occurred no imaging failure, the position alignment unit 505 uses the plurality of first scattered radiation reduction images to calculate the position alignment parameter in the same manner as described above (Step 607).

In FIG. 7, a long-length image obtained by performing the position alignment on a plurality of first scattered radiation reduction images is displayed on a position alignment screen 704. The position alignment screen 704 allows a user to correct the position alignment by performing input through the input unit 208 while examining the long-length image. The input unit 208 serves to input the positions of the first radiographic image subjected to the first processing and the second radiographic image subjected to the first processing.

On the position alignment screen 704, the long-length image obtained by combining the plurality of post-processed first scattered radiation reduction images is displayed. The position alignment unit 105 performs the position alignment on the first radiographic image and the second radiographic image based on the input positions. The combining unit 108 combines the first radiographic image and the second radiographic image that have been subjected to the first processing at the positions of the first radiographic image and the second radiographic image that have been subjected to the position alignment. For example, the combining unit 108 combines the first radiographic image and the second radiographic image that have been subjected to the first processing through the weighting based on the distance from the predetermined coordinate in the coordinate system of the first radiographic image and the second radiographic image that have been subjected to the position alignment.

The position alignment for the long-length image displayed at first is performed based on the positional information obtained from the hardware device, for example, the position sensor built in the standing posture imaging base or the table for external imaging that contains the radiation detection apparatus 202 or the position sensor built in the radiation detection apparatus 202. The position alignment unit 105 may perform the position alignment based on the positions of the radiation detection apparatus 401 and 402 measured by the position sensors.

When the position alignment is corrected by the input received from the input unit 208, positional information on the corrected position is calculated as the position alignment parameter. After the position alignment is appropriately performed, the control PC 201 advances the processing to Step 608.

Subsequently, the second scattered radiation estimation unit 506 subjects the pre-processed radiographic image to the second scattered radiation estimation that takes the influence of the adjacent radiation detection apparatus into consideration to generate the second scattered radiation image (Step 608). In the position alignment performed between the radiation detection apparatus 401 and 402 in the second scattered radiation estimation, the position alignment parameter calculated in Step 607 is used. In the second scattered radiation estimation, the detailed scattered radiation estimation that takes the scattered radiation from the adjacent radiation detection apparatus into consideration is performed in order to generate a highly-accurate long-length image to be used for diagnosis.

Subsequently, the second scattered radiation reduction unit 507 performs the second scattered radiation reduction (Step 609). The second scattered radiation image obtained in Step 608 is removed from the pre-processed radiographic image, to thereby generate the second scattered radiation reduction image.

Subsequently, in the same manner as described above, the combining unit 508 combines the plurality of second scattered radiation reduction images to generate the long-length image (Step 610). The position alignment parameter calculated in Step 607 is used to perform the position alignment on the plurality of second scattered radiation reduction images, and to perform the combining processing on the plurality of second scattered radiation reduction images based on an appropriate positional relationship between the second scattered radiation reduction images.

The post-processing unit 509 performs post-processing on the long-length image obtained by combining the second scattered radiation reduction images to generate a post-processed radiographic image (Step 611). The post-processing represents processing for generating an image optimal for diagnosis, and includes frequency processing or gradation processing.

Finally, the image output unit 510 outputs a post-processed radiation image to a display device (Step 612). Examples of the display device include a monitor, a film output device, and a PACS.

In this manner, it is determined whether or not the imaging has been appropriately performed, whether or not there is an imaging failure, and whether or not the position alignment has been appropriately performed based on the first scattered radiation reduction image generated by the simple scattered radiation estimation that does not take the scattered radiation from the adjacent radiation detection apparatus into consideration. As a result, the calculation cost is suppressed, while the first scattered radiation reduction image is output in less time, to thereby be able to start those kinds of determination at an early stage. Meanwhile, when the long-length image for diagnosis is generated, the detailed scattering radiation estimation that takes the scattered radiation from the adjacent radiation detection apparatus into consideration is performed by the second scattered radiation estimation, to thereby be able to output the second scattered radiation reduction image having high image quality.

Fourth Embodiment

An example of a fourth embodiment of the present invention is described in detail. Descriptions of the same configurations, functions, and operations as those of the above-mentioned embodiments are omitted, and different points from those of the above-mentioned embodiments are mainly described.

In the above-mentioned embodiment, the detailed scattering radiation estimation that takes the scattered radiation from the adjacent radiation detection apparatus into consideration is performed in the second scattered radiation estimation, but in the fourth embodiment, the simple scattered radiation estimation and the detailed scattered radiation estimation are switched depending on the kind of the image output unit 510 in the second scattered radiation estimation.

For example, when the image output unit 510 is a monitor or other such display device, the second scattered radiation estimation is the simple scattered radiation estimation that does not take the scattered radiation from the adjacent radiation detection apparatus into consideration. In this case, the first scattered radiation image calculated in the first scattered radiation estimation or the first scattered radiation reduction image may be used for the second scattered radiation estimation. In another case, the long-length image obtained by combining the first scattered radiation reduction images based on the position alignment parameter may be output to the monitor without performing the second scattered radiation estimation.

When the purpose of the image to be output to the monitor is to examine the image as the long-length image, the speed up of the display may meet a user's needs. In this case, the long-length image to be output to the monitor may be the long-length image generated by the simple scattered radiation estimation in the second scattered radiation estimation.

However, when details are to be examined with a magnified view, an unmagnified view, or the like during the examination of the image, the image is required to have high image quality. In this case, the second scattered radiation estimation may be switched to the detailed scattered radiation estimation to perform the processing again, and after the second scattered radiation estimation that takes the scattered radiation from the adjacent radiation detection apparatus into consideration is performed, the magnified view or the unmagnified view of the long-length image having high image quality may be provided. In this case, the display (for example, monitor 701) is capable of displaying the first radiographic image subjected to the second processing and the second radiographic image subjected to the second processing.

In another case, when the image output unit 510 is a PACS or an image recording medium, the long-length image having high image quality is output after the second scattered radiation estimation that takes the scattered radiation from the adjacent radiation detection apparatus into consideration is performed. When the purpose of the image to be output to the PACS or the image recording medium is to make use of the image for diagnosis, the image having high image quality meets the user's needs. The input unit 208 serves to input an instruction to switch the display or the output between the radiographic image subjected to the first processing and the radiographic image subjected to the second processing.

Fifth Embodiment

An example of a fifth embodiment of the present invention is described in detail. Descriptions of the same configurations, functions, and operations as those of the above-mentioned embodiments are omitted, and different points from those of the above-mentioned embodiments are mainly described.

In the above-mentioned embodiment, the first scattered radiation estimation and the second scattered radiation estimation are switched in the entire region of the adjacent imaging region or the region influenced by the scattering radiation from the adjacent radiation detection apparatus. However, the first scattered radiation estimation and the second scattered radiation estimation may be switched in a region in which the scattered radiation estimation is particularly difficult other than the above-mentioned regions.

Figure 8:
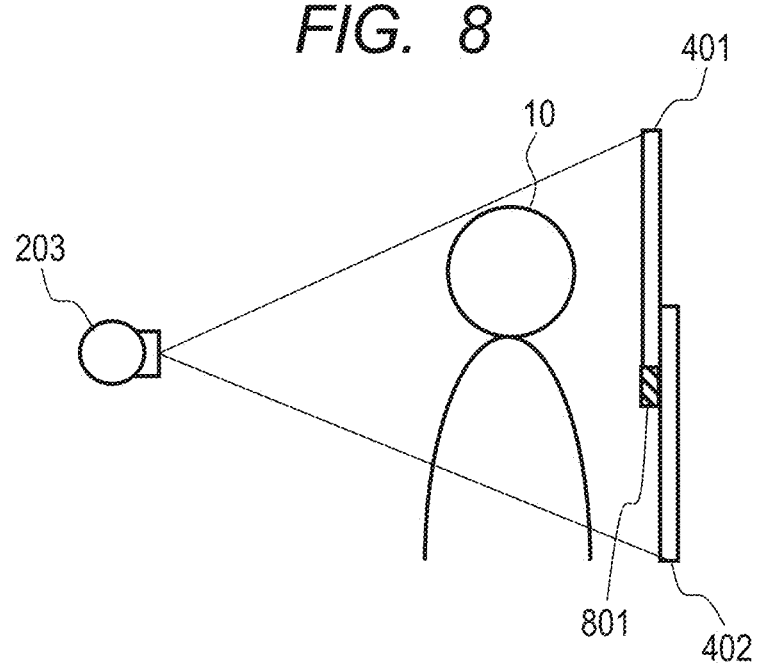
FIG. 8 is a diagram for illustrating an example of arranging a plurality of radiation detection apparatuses with an overlap for the long-length imaging.

As illustrated in FIG. 8, in the long-length imaging, the plurality of radiation detection apparatuses 401 and 402 are arranged with a partial overlap so as to have the overlapping region in the imaging region. Therefore, an image of a structure included in the radiation detection apparatus 401 arranged at a position closer to the radiation generation apparatus 203 is included in the imaging region of the radiation detection apparatus 402 arranged at a position farther from the radiation generation apparatus 203.

For example, when an image of a metallic portion 801 is included in the imaging region of the radiation detection apparatus 402 as the structure included in the radiation detection apparatus 401, the metallic portion 801 generates a larger amount of scattered radiation than other structures, and particularly degrades accuracy in position alignment. As a result, the first scattered radiation estimation and the second scattered radiation estimation are switched in the imaging region including the image of the structure included in the radiation detection apparatus, to thereby be able to improve the accuracy in scattered radiation estimation, and to enhance the accuracy in position alignment.

In addition, a kernel for scattered radiation estimation is used in the imaging region including the image of the structure included in the radiation detection apparatus, to thereby be able to improve the accuracy in scattered radiation estimation, and to enhance the accuracy in position alignment.

According to the first to fifth embodiments, it is possible to improve the accuracy in position alignment exhibited when a plurality of radiographic images are combined.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-044101, filed Mar. 8, 2017, which is hereby incorporated by reference herein in its entirety.

What is claimed is:

1. A radiation imaging apparatus, comprising:
a radiation detector configured to generate a first radiographic image and a second radiographic image based on a radiation;
a scattered radiation reduction unit configured to reduce a scattered radiation component by performing image processing on the first radiographic image and the second radiographic image;
a position alignment unit configured to perform position alignment on the first radiographic image and the second radiographic image, using the first radiographic image and the second radiographic image from which the scattered radiation component has been reduced;
a combining unit configured to combine the first radiographic image and the second radiographic image that have been subjected to the position alignment; and
a scattered radiation estimation unit configured to use a positional relationship between the first radiographic image and the second radiographic image that have been subjected to the position alignment to estimate the scattered radiation component of a radiographic image of at least one of the first radiographic image or the second radiographic image based on the first radiographic image and the second radiographic image that have been subjected to the position alignment,
wherein the scattered radiation reduction unit is configured to remove the estimated scattered radiation component from the radiographic image of at least one of the first radiographic image or the second radiographic image.

2. A radiation imaging apparatus according to claim 1, wherein:
the scattered radiation reduction unit is configured to perform first processing for reducing the scattered radiation component from the first radiographic image and the second radiographic image;
the position alignment unit is configured to perform the position alignment on the first radiographic image and the second radiographic image, using the first radiographic image subjected to the first processing and the second radiographic image subjected to the first processing;
the scattered radiation estimation unit is configured to use the positional relationship between the first radiographic image and the second radiographic image that have been subjected to the position alignment to estimate the scattered radiation component of the radiographic image of at least one of the first radiographic image or the second radiographic image based on the first radiographic image and the second radiographic image that have been subjected to the position alignment; and
the scattered radiation reduction unit is configured to perform second processing for removing the estimated scattered radiation component from the radiographic image of at least one of the first radiographic image or the second radiographic image.

3. A radiation imaging apparatus according to claim 2, wherein the first processing includes estimating a first scattered radiation component of the first radiographic image based on the first radiographic image, and removing the first scattered radiation component from the first radiographic image, to thereby reduce the scattered radiation component from the first radiographic image.

4. A radiation imaging apparatus according to claim 2, wherein the second processing includes estimating a second scattered radiation component of the first radiographic image based on the first radiographic image and the second radiographic image that have been subjected to the position alignment, and removing the second scattered radiation component from the first radiographic image, to thereby reduce the scattered radiation component from the first radiographic image.

5. A radiation imaging apparatus according to claim 2, wherein:
the position alignment unit is configured to perform the position alignment on the first radiographic image and the second radiographic image, using the first radiographic image and the second radiographic image;
the scattered radiation estimation unit is configured to use the positional relationship between the first radiographic image and the second radiographic image that have been subjected to the position alignment to estimate a first scattered radiation component of the first radiographic image based on the first radiographic image and the second radiographic image that have been subjected to the position alignment; and
the scattered radiation reduction unit is configured to perform the first processing for removing the first scattered radiation component from the first radiographic image.

6. A radiation imaging apparatus according to claim 1, wherein the position alignment unit is configured to perform the position alignment so that images of an overlapping region corresponding to an overlap between imaging regions of the first radiographic image and the second radiographic image match each other.

7. A radiation imaging apparatus according to claim 1, wherein the position alignment unit is configured to perform the position alignment based on a position of the radiation detector measured by a position sensor.

8. A radiation imaging apparatus according to claim 2, wherein the scattered radiation reduction unit is configured to, in the second processing:
remove a first scattered radiation component estimated based on the first radiographic image from the first radiographic image at a position that exceeds a predetermined range from a position of the second radiographic image subjected to the position alignment; and remove a second scattered radiation component estimated based on the first radiographic image and the second radiographic image that have been subjected to the position alignment from the first radiographic image at a position within the predetermined range from the position of the second radiographic image subjected to the position alignment.

9. A radiation imaging apparatus according to claim 2, wherein the scattered radiation reduction unit is configured to, in the second processing:

remove a first scattered radiation component estimated based on the first radiographic image from the first radiographic image at a position that exceeds a predetermined range from an overlapping region corresponding to an overlap between imaging regions of the first radiographic image and the second radiographic image that have been subjected to the position alignment; and remove a second scattered radiation component estimated based on the first radiographic image and the second radiographic image that have been subjected to the position alignment from the first radiographic image at a position within the predetermined range from the overlapping region.

10. A radiation imaging apparatus according to claim 2, further comprising a display configured to enable display of the first radiographic image subjected to the first processing and the second radiographic image subjected to the first processing.

11. A radiation imaging apparatus according to claim 2, further comprising an input unit configured to input an instruction to switch one of display and output between the radiographic image subjected to the first processing and the radiographic image subjected to the second processing.

12. A radiation imaging apparatus according to claim 10, further comprising an input unit configured to input positions of the first radiographic image subjected to the first processing and the second radiographic image subjected to the first processing, wherein the position alignment unit is configured to perform the position alignment on the first radiographic image and the second radiographic image based on the input positions.

13. A radiation imaging apparatus according to claim 1, wherein the combining unit is configured to combine the first radiographic image and the second radiographic image through weighting based on a distance from a predetermined coordinate in a coordinate system of the first radiographic image and the second radiographic image that have been subjected to the position alignment.

14. A radiation imaging apparatus according to claim 13, wherein:

the predetermined coordinate indicates a center of an overlapping region corresponding to an overlap between imaging regions of the first radiographic image and the second radiographic image; and the distance includes a distance in a direction parallel to at least one of: an arrangement direction of the first radiographic image and the second radiographic image; a short-side direction of the overlapping region; or a direction of a straight line that connects centers of the first radiographic image and the second radiographic image.

15. A radiation imaging system, comprising:

a radiation generation unit configured to generate a radiation;

a radiation detector configured to generate a first radiographic image and a second radiographic image based on the radiation;

a scattered radiation reduction unit configured to reduce a scattered radiation component by performing image processing on the first radiographic image and the second radiographic image;

a position alignment unit configured to perform position alignment on the first radiographic image and the second radiographic image, using the first radiographic image and the second radiographic image from which the scattered radiation component has been reduced;

a combining unit configured to combine the first radiographic image and the second radiographic image that have been subjected to the position alignment and a scattered radiation estimation unit configured to use a positional relationship between the first radiographic image and the second radiographic image that have been subjected to the position alignment to estimate the scattered radiation component of a radiographic image of at least one of the first radiographic image or the second radiographic image based on the first radiographic image and the second radiographic image that have been subjected to the position alignment, wherein the scattered radiation reduction unit is configured to remove the estimated scattered radiation component from the radiographic image of at least one of the first radiographic image or the second radiographic image.

16. A radiation imaging method, comprising:

generating a first radiographic image and a second radiographic image based on a radiation;

reducing a scattered radiation component by performing image processing on the first radiographic image and the second radiographic image;

performing position alignment on the first radiographic image and the second radiographic image, using the first radiographic image and the second radiographic image from which the scattered radiation component has been reduced;

combining the first radiographic image and the second radiographic image that have been subjected to the position alignment; and using a positional relationship between the first radiographic image and the second radiographic image that have been subjected to the position alignment to estimate the scattered radiation component of a radiographic image of at least one of the first radiographic image or the second radiographic image based on the first radiographic image and the second radiographic image that have been subjected to the position alignment, wherein reducing the scattered radiation component includes removing the estimated scattered radiation component from the radiographic image of at least one of the first radiographic image or the second radiographic image.

17. A non-transitory computer-readable medium having stored thereon a program for causing a processor to execute each processing step of the radiation imaging method of claim 16 when the program is executed by the processor.

* * * * *